US008762303B2

(12) United States Patent
Zhao et al.

(10) Patent No.: US 8,762,303 B2
(45) Date of Patent: Jun. 24, 2014

(54) METHODS FOR FEATURE SELECTION USING CLASSIFIER ENSEMBLE BASED GENETIC ALGORITHMS

(75) Inventors: Luyin Zhao, Belleville, NY (US); Lilla Boroczky, Mount Kisco, NY (US); Lalitha A. Agnihotri, Tarrytown, NY (US); Michael C. Lee, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 928 days.

(21) Appl. No.: 12/441,956

(22) PCT Filed: Sep. 17, 2007

(86) PCT No.: PCT/IB2007/053750
§ 371 (c)(1),
(2), (4) Date: Oct. 23, 2009

(87) PCT Pub. No.: WO2008/035276
PCT Pub. Date: Mar. 27, 2008

(65) Prior Publication Data
US 2010/0036782 A1 Feb. 11, 2010

Related U.S. Application Data

(60) Provisional application No. 60/826,593, filed on Sep. 22, 2006, provisional application No. 60/884,288, filed on Jan. 10, 2007.

(51) Int. Cl.
*G06N 3/12* (2006.01)
(52) U.S. Cl.
USPC .......................................................... 706/13

(58) Field of Classification Search
CPC ......... G06N 3/126; G06N 3/086; G06N 3/12; G06N 99/005; G06N 7/005; G06N 13/0265
See application file for complete search history.

(56) References Cited

U.S. PATENT DOCUMENTS

| 5,513,101 A | 4/1996 | Pinsky et al. |
| 2004/0111384 A1 | 6/2004 | Shin et al. |
| 2006/0129324 A1* | 6/2006 | Rabinoff et al. ................ 702/19 |

FOREIGN PATENT DOCUMENTS

WO 9514977 A1 6/1995

OTHER PUBLICATIONS

Optiz, "Feature Selection for Ensembles", Proceedings Sixteenth National Conference on Artificial Intelligence, 1999, pp. 1-6.*
Boroczky et al, "Feature Subset Selection for Improving the Performance of False Positive Reduction in Lung Nodule Cad", IEEE Transactions on Information Technology in Biomedicine, vol. 10, No. 3, Jul. 2006, pp. 504-511.*
Kuncheva et al, "Designing Classifier Fusion Systems by Genetic Algorithms", IEEE Transactions on Evolutionary Computation, vol. 4, No. 4, 2000, pp. 327-336.*

(Continued)

*Primary Examiner* — Jeffrey A Gaffin
*Assistant Examiner* — Paulinho E Smith

(57) ABSTRACT

Methods for performing genetic algorithm-based feature selection are provided herein. In certain embodiments, the methods include steps of applying multiple data splitting patterns to a learning data set to build multiple classifiers to obtain at least one classification result; integrating the at least one classification result from the multiple classifiers to obtain an integrated accuracy result; and outputting the integrated accuracy result to a genetic algorithm as a fitness value for a candidate feature subset, in which genetic algorithm-based feature selection is performed.

19 Claims, 2 Drawing Sheets

(56) References Cited

OTHER PUBLICATIONS

Kuncheva et al., "Limits on the Majority Vote Accuracy in Classifier Fusion", Pattern Analysis Application, 2003, vol. 6, pp. 22-31.*
Svetnik et al., "Random Forest: A Classification and Regression Tool for Compound Classificaiton and QSAR Modeling", 2003, Journal of Chemical Inf. COmputer Science, vol. 43, pp. 1947-1958.*
Optiz et al, "Popular Ensemble Methods: An Empirical Study" Journal of Artificial Intelligence Research 11, 1999, pp. 169-198.
Zhang et al, "Neural vs. Statistical Classifier in Conjunction With Genetic Algorithm Based Ffeature Selection", Pattern Recobnition Letters Elsevier Netherlands, vol. 26, No. 7, May 15, 2005, pp. 909-919.
Miller, "Genetic Algorithms, Selection Schemes, and the Varying Effects of Noise", Evolutionary Computation 4(2), 1996, pp. 113-131.
Optiz, "Feature Selection for Ensembles", Proceedings Sixteenth National Conference on Artificial Intelligence, 1999, pp. 379-384.

Miller et al, "Feature Selection for Computer-Aided Polyp Detection Using Genetic Algorithms", Proceedings of the SPIE—The International Society for Optical Engineering, vol. 5031, 2003, pp. 102-110.
Yu et al, Ensemble Based on GA Wrapper Feature Selection Computers & Industrial Engineering Elsevier UK, vol. 51, No. 1, Sep. 2006, pp. 111-116.
Kuncheva, "A Theoretical Study on Six Classifier Fusion Strategies", IEEE Transactions on Pattern Analysis and Machine Intelligence, vol. 24, No. 2, Feb. 2002, pp. 281-286.
Morita et al, "Unsupervised Feature Selection for Ensemble of Classifiers", Proceedings Ninth International Workshop on Frontiers in Handwriting Recognition IEEE Comput. Soc Los Alamitos, CA, 2004, pp. 81-86.
Mehul P. Sampat et al, "Computer-Aided Detection and Diagnosis in Mammography", Handbook of Image and Video Processing, 2004, pp. 1195-1217.
Guerra-Salcedo et al, "Genetic Approach to Feature Selection for Ensemble Creation", Proceedings of Genetic and Evolutionary Computation Conference, 1999, pp. 236-243.

* cited by examiner

METHODS FOR FEATURE SELECTION USING CLASSIFIER ENSEMBLE BASED GENETIC ALGORITHMS

This application claims the benefit of U.S. provisional application Ser. No. 60/826,593 filed Sep. 22, 2006, which is incorporated herein in whole by reference.

Methods are provided for feature selection using genetic algorithms.

A genetic algorithm (GA) is a class of evolutionary algorithms used in computing as a search technique to find solutions to optimization and search problems. GA uses terminology and concepts to develop techniques inspired by evolutionary biology, including concepts such as inheritance, mutation, selection, and crossover.

Feature selection, also known as subset selection or variable selection, is a method used in machine learning. Prior to applying a learning algorithm to a dataset, a subset of the features available from the dataset is selected. The process of feature selection is used because it is computationally infeasible to use all available features in a dataset. Feature selection is also used to minimize problems of estimation and overfitting when a dataset has limited data samples containing a large number of features.

A typical domain for which feature selection is utilized is computer-aided diagnosis (CADx). CADx is a method that uses machine learning technology to predict a medical outcome, for example, to classify unknown lesions as malignant or benign. For example, in computed tomography (CT) imaging of the lung for lung cancer diagnosis, these input features may include the results of image processing algorithms as applied to the lung nodule under investigation. Improving the diagnostic accuracy of CADx systems is a key step to successful introduction of this technology into the clinic.

Due to the large number of image features and clinical features that might be computed and retrieved for each lesion, feature selection is an important step due to infeasibility of using all available features in a dataset and problems of estimation when a dataset has limited data samples containing a large number of features. Feature selection using GA and support vector machines (SVM) has been shown to be an efficient feature selection method for computer-aided detection (CAD; Boroczky et al., IEEE Transaction on Biomedical Engineering, 10(3), pp. 504-551, 2006).

Although GA-based feature selection has shown to be successful in a number of areas, problems and biases often occur due to noisy and small medical datasets. This is caused by random splitting inside GA, which can generate biased training datasets and biased testing datasets from a learning data set.

Accordingly, methods are provided herein for performing genetic algorithm-based feature selection. The methods in one embodiment include steps of applying multiple data splitting patterns to a learning data set to build multiple classifiers to obtain at least one classification result; integrating the at least one classification result from the multiple classifiers to obtain an integrated accuracy result; and outputting the integrated accuracy result to a genetic algorithm as a fitness value for a candidate feature subset, where genetic algorithm-based feature selection is performed.

A related embodiment further includes using the genetic algorithm to obtain the candidate feature subset.

In a related embodiment, the multiple data splitting patterns divide the learning data set into training data and testing data. Learning data sets are used to tune parameters of a learning rule. A training data set includes an input vector (including the available features) and an answer vector (including known diagnosis, i.e. malignant/benign), and is used together with a supervised learning method to train the computer using a database having the cases and the known diagnoses. A testing data set includes known examples that are used to test the performance of the classifier built on the training data.

In another related embodiment, the multiple classifiers are selected from at least one of a support vector machine, a decision tree, linear discriminant analysis, and a neural network.

In another related embodiment, building the multiple classifiers further includes using a re-sampling technique to obtain each of a plurality of training sets and a plurality of testing sets from the learning data set.

In yet another related embodiment, building the multiple classifiers further includes using a plurality of training sets.

In another embodiment, the method further includes combining classification results from the multiple classifiers to form a group prediction.

In a related embodiment, integrating at least one classification result further includes calculating at least one result selected from the group of an average, a weighted average, a majority vote, a weighted majority vote, and a median value.

In another related embodiment, the method further includes using a genetic algorithm to repetitively evaluate candidate feature subsets using the fitness values, to generate new candidate feature subsets, and obtain an optimal final feature subset.

In a related embodiment, the method is used in a medical imaging modality selected from the group of at least one of CT, MRI, X-ray and ultrasound.

In another embodiment, the method is used in computer aided detection (CAD). In a related embodiment, the method is used in CAD of a disease selected from the group of at least one of lung cancer, breast cancer, prostate cancer and colorectal cancer.

In yet another embodiment, the method is used in computer aided diagnosis (CADx). In a related embodiment, the method is used in CADx of a disease selected from the group of at least one of lung cancer, breast cancer, prostate cancer and colorectal cancer.

The methods provided herein integrate classifier ensemble methods into an evolutionary feature selection process to improve GA-based feature selection. The GA evaluates each feature subset using an integrated predictive result based on multiple data splitting patterns, rather than evaluating a single data splitting pattern. This is especially useful for noisy data that may otherwise cause a biased fitness value calculation.

Feature selection is used in determining an optimal feature subset in order to build a classifier. A GA and SVM-based feature selection process is used. A classifier is built based on an optimal feature subset.

Classifiers are used in CAD and CADx of different diseases, for example for lung cancer and other types of cancer having solid tumors. In the field of machine learning, classifiers are used to group items that have similar feature values. Possible classifiers include SVMs, decision trees, linear discriminant analysis and neural networks. SVMs are linear classifiers, and are often used since they have shown superior performance with respect to classifiers. A decision tree is a predictive model that maps observations about an item to conclusions about that item's target value. Linear discriminant analysis is used to find the linear combination of features which best separates two or more classes of objects or event. The resulting combinations are used as a linear classifier or in dimensionality reduction before later classification. A neural network is a non-linear statistical data modeling tools that are used to model relationships between inputs and outputs and/or to find patterns in data.

A CADx system that provides high confidence to clinicians improves clinician workflow by providing fast and accurate diagnosis (fewer false positives and false negatives). A CADx system can be used as a second reader to increase clinicians' confidence in their diagnosis, leading to significant reduction of unnecessary biopsies of lung lesions such as nodules, and leading to a significant reduction of unnecessary delay of treatment. Furthermore, a CADx system can facilitate lung cancer screening of asymptomatic patients since diagnosis can be reached quickly and accurately. MSCT scanners, exemplified by but not limited to the Philips Brilliance series, offer increasing resolution and allow finer structures to be observed while producing increasing amounts of image data to be interpreted by radiologists.

In the machine learning based CADx domain, one of the most common problems is that training data are usually noisy. Noise is especially prevalent when a training data set is not sufficiently large. This has a substantial impact on feature selection effectiveness. Since GA relies on random data splitting to evaluate each chromosome representing a feature subset, noisy data gives an inaccurate evaluation of how a feature subset performs. As a result, a good feature subset can be discarded due to its performance on a "bad" random data splitting. This subsequently affects the successful convergence to an optimal feature subset.

Figure 1:
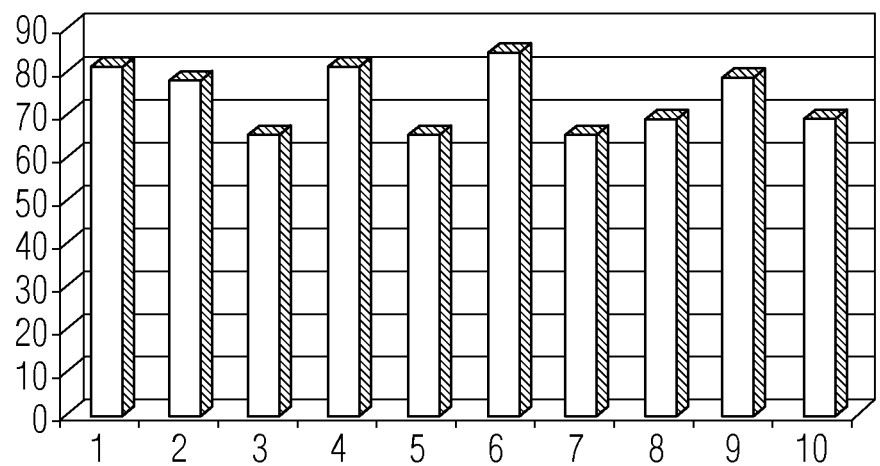
FIG. 1 is a bar graph that shows the impact of data splitting on classification accuracy.

FIG. 1 shows a graph of results of an experiment using data from 129 cases of lung cancer. A randomly selected data subset was used for training, i.e. building a SVM classifier, and the remaining data was used for testing. This is known as data splitting. The result in FIG. 1 shows that when a different data splitting is used, the classification accuracy, i.e. testing accuracy, differs significantly.

Previous methods typically assume that a noise component is randomly drawn from an unbiased, i.e. mean of zero, normal distribution. The fitness value is typically corrected by estimating the noise bias and subtracting it from the fitness value (Miller et al., Evolutionary Computation, 1996, available at http://leitl.org/docs/ecj96.ps.gz). A fitness value is an objective measure of the quality of a solution.

Not all data in the real world has an unbiased distribution, or the bias is difficult to estimate. To address these problems, the methods provided herein use classifier ensembles to reduce the impact of noise when evaluating a feature subset during GA evolution.

Classifier ensemble has been theoretically and empirically proven to be more accurate than any of the individual classifiers making up the ensembles (Opitz et al., Journal of Artificial Intelligence Research, pp. 169-198, 1999). The methods provided herein use the following variances: reliance on re-sampling techniques to obtain different training sets for building multiple classifiers, and use of multiple feature subsets to build multiple classifiers. Classification results from the multiple classifiers are combined together to form a group prediction.

Instead of building one classifier (i.e. using one data splitting pattern) according to prior methods to evaluate the performance of a feature subset, the methods provided herein build multiple classifiers, also known as an ensemble, and integrate the classification results from these classifiers. In this case, several classifiers are built on different data splits. Each classifier will result in a decision, e.g. whether a lesion is malignant or benign. The integration method can be a majority vote, i.e. the prediction selected by most member classifiers. Alternative integration methods include calculating an average, a weighted average, or a median value (Kuncheva, L. I., IEEE Transactions on Pattern Analysis and Machine Intelligence, 24(2), pp. 281-286, 2002). The accuracy obtained by the classifier ensemble is better than any single classifier. The integrated accuracy, as determined by the classifier ensemble, is returned to the GA as a fitness value for one specific feature subset.

Figure 2:
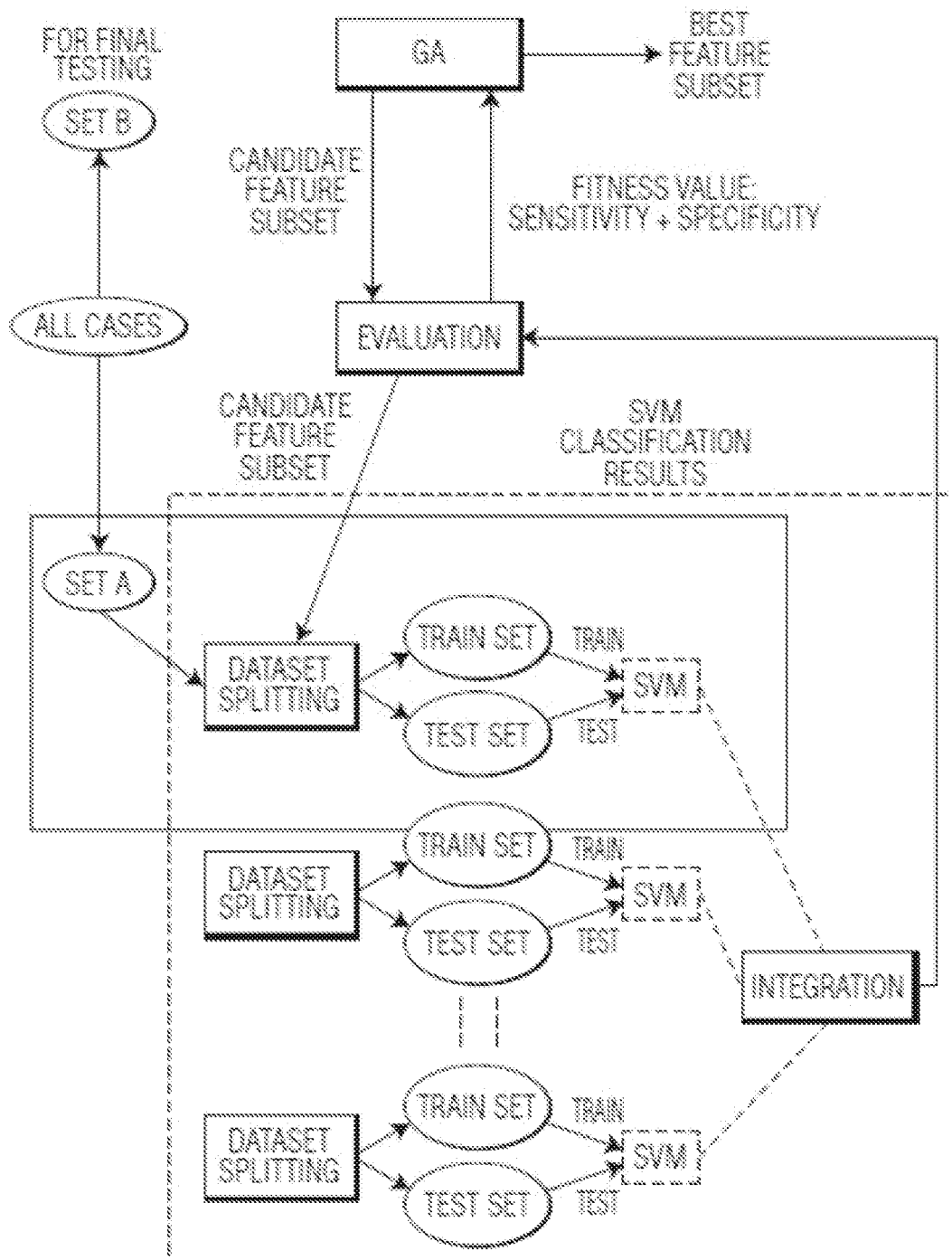
FIG. 2 is a flowchart that shows steps in building multiple classifiers to analyze a dataset and obtain a best feature subset.

FIG. 2 shows data samples split into two sets, Set A (the learning data set) and Set B (the data set reserved for final testing). Set A undergoes data splitting, dividing the Set A data into a Training Set and a Test Set. Multiple data splitting patterns are applied to build multiple classifiers, i.e. SVM. The results from the multiple classifiers are integrated and evaluated. Accuracy of classification is performed on the test set data, which is part of the original dataset. The results of the accuracy of classification, which are the integrated results from each classifier, are returned to the GA as a fitness value for a candidate feature subset. The fitness value can include both specificity and sensitivity. After the integrated results are returned to the GA, the GA determines which features are retained/discarded and generates new candidate feature subset(s) through internal mutation and crossover operations. The GA evolutionary process repeats until termination criteria is reached, when the best feature subset is determined.

The methods provided herein can be used with several imaging modalities, for example MRI, CT, X-ray or ultrasound. The methods provided herein are applied to medical imaging modalities, including imaging modalities that are used for detecting and diagnosing abnormal lesions in the human body, for example, data collected from imaging systems, i.e. electronic scanners. The methods and systems provided herein can be used in radiology workstations, exemplified but not limited to Philips Extended Brilliance Workstation, Philips Mx8000, and the Philips Brilliance CT scanner series or incorporated into PACS systems exemplified but not limited to Stentor iSite systems. The invention provided herein is also used in CAD and CADx. When applied to CAD and CADx, the invention provided herein is used to detect and diagnose diseases such as lung cancer, colon polyps, colorectal cancer, prostate cancer, and breast cancer and other cancerous and non-cancerous lesions.

It will furthermore be apparent that other and further forms of the invention, and embodiments other than the specific and exemplary embodiments described above, may be devised without departing from the spirit and scope of the appended claims and their equivalents, and therefore it is intended that the scope of this invention encompasses these equivalents and that the description and claims are intended to be exemplary and should not be construed as further limiting. The contents of all references cited herein are incorporated by reference.

What is claimed is:

1. A method for performing genetic algorithm-based feature selection, the method comprising:
dividing a set of data samples into at least a first sub-set of data samples and a second sub-set of data samples, wherein the first sub-set of data samples and the second sub-set of data samples include different sub-sets of the set of data samples;
applying a data splitting pattern to the first sub-set of data samples, splitting the first sub-set of data samples into a first training set of data samples and a first testing set of data samples, wherein the first training set of data samples and the first testing set of data samples include different data samples of the first sub-set of data samples;

creating a first classifier based on the first training set of data samples and the first testing set of data samples;

applying one or more different data splitting patterns to the first sub-set of data samples, splitting the first sub-set of data samples into one or more training sets of data samples and one or more testing sets of data samples, wherein the one or more training sets of data samples and the corresponding one or more testing sets of data samples include different data samples of the first sub-set of data samples;

creating one or more classifiers based on the one or more training sets of data samples and the corresponding one or more testing sets of data samples;

integrating the first classifier and the one or more classifiers, generating an integrated classifier; and outputting the integrated classifier to a genetic algorithm as a fitness value for a candidate feature subset, wherein genetic algorithm-based feature selection is performed using the integrated classifier.

2. The method according to claim 1, further comprising using the genetic algorithm to obtain the candidate feature subset.

3. The method according to claim 1, wherein the first classifier and the one or more classifiers are selected from the group consisting of at least one of a support vector machine, a decision tree, linear discriminant analysis, and a neural network.

4. The method according to claim 1, further comprising:
using a re-sampling technique to obtain the first training and the one or more training sets of data samples and the first testing and the one or more testing sets of data samples from the first sub-set of data samples.

5. The method according to claim 1, further comprising combining classification results from the first classifier and the one or more classifiers to form a group prediction.

6. The method according to claim 1, wherein integrating the first classifier and the one or more classifiers further comprises calculating at least one result selected from a group consisting of an average, a weighted average, and a weighted majority vote.

7. The method according to claim 1, further comprising using the genetic algorithm to obtain an optimal final feature subset.

8. The method according to claim 1, wherein the method is used in a medical imaging modality selected from a group consisting of at least one of CT, MRI, X-ray and ultrasound.

9. The method according to claim 1, wherein the method is used in computer aided detection (CAD).

10. The method according to claim 9, wherein the method is used in CAD of a disease selected from a group consisting of at least one of lung cancer, breast cancer, prostate cancer and colorectal cancer.

11. The method according to claim 1, wherein the method is used in computer aided diagnosis (CADx).

12. The method according to claim 11, wherein the method is used in CADx of a disease selected from a group consisting of at least one of lung cancer, breast cancer, prostate cancer and colorectal cancer.

13. The method according to claim 1, further comprising:
evaluating the integrated classifier by performing an accuracy of classification of the integrated classifier using the second sub-set of data samples;

generating an evaluation result, which are the integrated results from each classifier; and outputting the evaluation result to the genetic algorithm as the fitness value for the candidate feature subset.

14. The method according to claim 1, wherein the fitness value includes specificity.

15. The method according to claim 1, wherein the fitness value includes sensitivity.

16. The method according to claim 1, wherein the fitness value includes both specificity and sensitivity.

17. The method according to claim 1, further comprising:
determining, with the genetic algorithm, features to retain and features to discard.

18. The method according to claim 1, further comprising:
generating, with the genetic algorithm, a subsequent set of data samples through mutation and crossover operations.

19. The method according to claim 18, further comprising:
splitting the subsequent set of data samples into at least a first sub-set of the subsequent set of data samples and a second sub-set of the subsequent set of data samples, wherein the first sub-set of the subsequent set of data samples and the second sub-set of the subsequent set of data samples include different sub-sets of the subsequent set of data samples;

applying a subsequent data splitting pattern to the first sub-set of the subsequent set of data samples, splitting the first sub-set of the subsequent set of data samples into a first training set of the subsequent set of data samples and a first testing set of the subsequent set of data samples, wherein the first training set of the subsequent set of data samples and the first testing set of the subsequent set of data samples include different data samples of the first sub-set of the subsequent set of data samples;

creating a subsequent first classifier based on the first training set of the subsequent set of data samples and the first testing set of the subsequent set of data samples;

applying one or more different subsequent data splitting patterns to the first sub-set of the subsequent set of data samples, splitting the first sub-set of the subsequent set of data samples into one or more subsequent training sets of the subsequent set of data samples and one or more subsequent testing sets of the subsequent set of data samples, wherein the one or more subsequent training sets of the subsequent set of data samples and the corresponding one or more subsequent testing sets of the subsequent set of data samples include different data samples of the first sub-set of the subsequent set of data samples;

creating one or more subsequent classifiers based on the one or more training sets of the subsequent set of data samples and the corresponding one or more subsequent testing sets of the subsequent set of data samples;

integrating the first subsequent classifier and the one or more subsequent classifiers, generating a subsequent integrated classifier; and outputting the subsequent integrated classifier to the genetic algorithm as the fitness value for the candidate feature subset, wherein subsequent genetic algorithm-based feature selection is performed using the subsequent integrated classifier.

* * * * *

UNITED STATES PATENT AND TRADEMARK OFFICE
CERTIFICATE OF CORRECTION

| | |
|---|---|
| PATENT NO. | : 8,762,303 B2 |
| APPLICATION NO. | : 12/441956 |
| DATED | : June 24, 2014 |
| INVENTOR(S) | : Zhao et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this
Eleventh Day of August, 2015

Michelle K. Lee
*Director of the United States Patent and Trademark Office*